(12) United States Patent
Sambusseti

(10) Patent No.: US 9,044,310 B2
(45) Date of Patent: Jun. 2, 2015

(54) ORTHOTOPIC ARTIFICIAL BLADDER PROSTHESIS

(76) Inventor: Antonio Sambusseti, Cremona (IT)

( * ) Notice: Subject to any disclaimer, the term of this patent is extended or adjusted under 35 U.S.C. 154(b) by 8 days.

(21) Appl. No.: 13/805,502

(22) PCT Filed: Apr. 28, 2011

(86) PCT No.: PCT/EP2011/056785
§ 371 (c)(1),
(2), (4) Date: Dec. 19, 2012

(87) PCT Pub. No.: WO2011/160875
PCT Pub. Date: Dec. 29, 2011

(65) Prior Publication Data
US 2013/0103164 A1 Apr. 25, 2013

(30) Foreign Application Priority Data
Jun. 25, 2010 (IT) .............................. MI2010A1164

(51) Int. Cl.
*A61F 2/04* (2013.01)
*A61F 2/06* (2013.01)
(52) U.S. Cl.
CPC . *A61F 2/04* (2013.01); *A61F 2/042* (2013.01); *A61F 2/064* (2013.01)
(58) Field of Classification Search
CPC ........................................................ A61F 2/04

USPC ................... 623/23.64–23.68; 600/2, 29–31; 604/257, 258, 327–329
See application file for complete search history.

(56) References Cited

U.S. PATENT DOCUMENTS

| 4,015,478 A * | 4/1977 | Schmaus .......................... 73/741 |
| 2002/0077661 A1 | 6/2002 | Saadat |
| 2002/0151913 A1 | 10/2002 | Berg et al. |
| 2011/0230964 A1* | 9/2011 | Yacoub et al. .................... 623/8 |

FOREIGN PATENT DOCUMENTS

| FR | 2 347 031 A1 | 11/1977 |
| WO | 03/028546 A2 | 4/2003 |
| WO | 2007039159 A1 | 4/2007 |
| WO | 2009/077047 A1 | 6/2009 |

OTHER PUBLICATIONS

International Search Report, dated May 24, 2011, from corresponding PCT application.

* cited by examiner

*Primary Examiner* — Yashita Sharma
(74) *Attorney, Agent, or Firm* — Young & Thompson

(57) ABSTRACT

An orthotopic prosthesis (1) of artificial bladder includes a balloon (600), two hollow elements (300) for the forced fitting of ureters (6,6') and a frustoconical element (602) for the connection of the urethra (8) to the prosthesis in the absence of stitches.

18 Claims, 5 Drawing Sheets

FIG. 1f
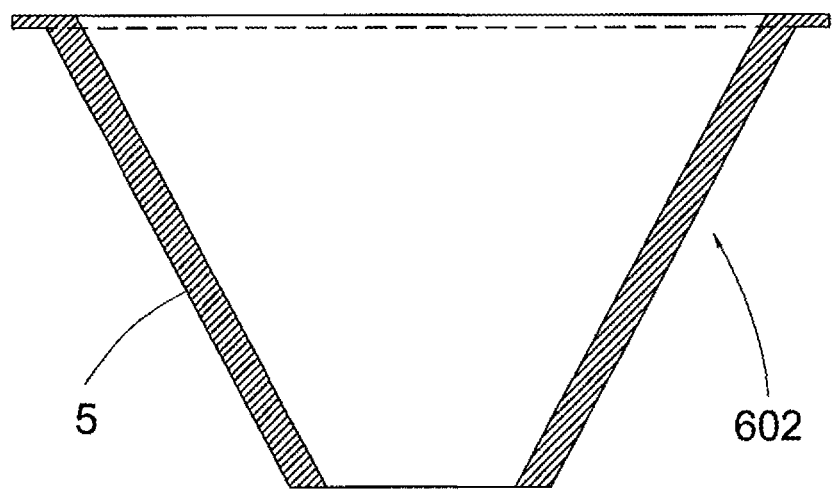
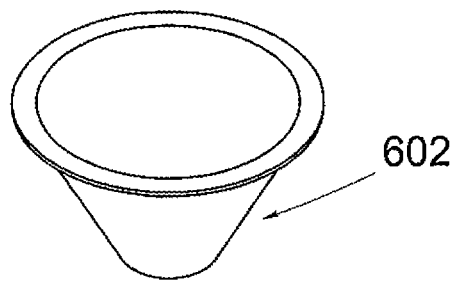
FIG. 1g
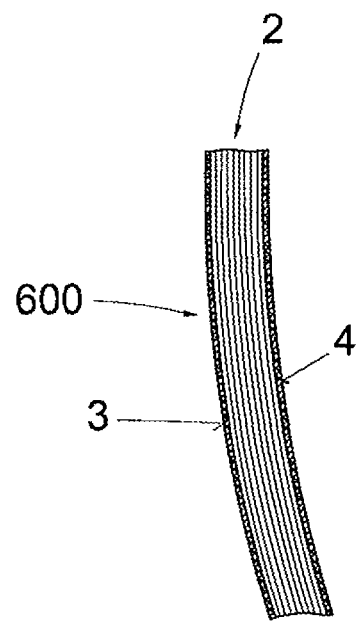
FIG. 2
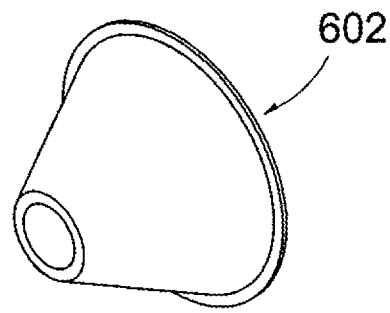
FIG. 1h

ORTHOTOPIC ARTIFICIAL BLADDER PROSTHESIS

BACKGROUND OF THE INVENTION

The present invention relates to an improved orthotopic artificial bladder prosthesis provided with elements for connection to the ureters and urethra.

DESCRIPTION OF THE RELATED ART

As is known, when a patient's bladder is affected by serious, incurable pathologies which jeopardise the proper functioning thereof, its replacement with an artificial bladder prosthesis is desirable.

The various solutions developed to solve the problem include replacement of the natural bladder with a compressible bladder made of soft multilayer silicone whose emptying takes place by simple compression of the lower abdomen, as described in the patent application WO 2007/039159.

This type of prosthesis provides for the connection between said artificial bladder and the ureters and urethra to be made by the use of stitches. However attachment with stitches cannot always be adopted, such as for example in the case wherein the ureters and/or urethra are weakened and/or thinned for congenital or pathological reasons. Moreover the use of stitches requires high manual skill and a considerable length of time during the replacement procedure.

SUMMARY OF THE INVENTION

The object of the present invention is to eliminate the disadvantages of the prior art, providing an orthotopic artificial bladder prosthesis which is able to replace the natural bladder and which allows a considerable improvement in the quality of life of the patient.

Another object of the present invention is to provide such an orthotopic artificial bladder prosthesis which does not require the use of stitches for attaching the ureters and/or urethra to said artificial bladder and is able to ensure at the same time optimal attachment of the same without any risk of detachment of the ureters/urethra from said bladder.

Yet another object of the present invention is to provide such an orthotopic artificial bladder prosthesis which is simple to manufacture and with improved biocompatibility and reduced rejection.

These objects are achieved by the artificial bladder in accordance with the invention having the features listed in the annexed independent claim 1.

Advantageous embodiments of the invention are disclosed by the dependent claims.

The orthotopic artificial bladder prosthesis according to the invention therefore comprises a casing in the form of a sac or balloon, made of a multilayer membrane in soft and elastic synthetic material, which is rendered bio compatible by means of an internal and external coating made of a specific material.

In particular said prosthesis is made with a radiopaque material suitable for being viewed in X ray plates, ultrasound scans and other systems of analysis which adopt radio waves. Moreover the inner surface of said prosthesis is coated with a material adapted not to deteriorate with urine while the outer surface is coated with a material designed to prevent fusion of said prosthesis with the surrounding tissues.

Said orthotopic prosthesis also comprises at least two holes for the connection of the ureters which takes place by means of the same number of hollow tubular elements: each element is formed by a base and by a tubular portion having an internal diameter substantially equal to the diameter of the ureters which is suitable for passing through the holes present in the prosthesis. Each ureter is then fitted forcedly inside said tubular portion of each hollow element mounted on the prosthesis.

Each tubular element therefore represents a portion of a hollow conic element. Said tubular element is connected to a frustoconical portion having a widened base which is suitable for being glued to the inner surface of said balloon so as to render said hollow conic element integral with said balloon.

Said hollow conic elements are also highly biocompatible and also provided internally with one or more projections adapted to avoid possible withdrawal and detachment of said ureters since, following their fitting in said hollow elements, they are tensioned.

A third hole is also provided for connection of the urethra to said prosthesis by means of a respective hollow conical frustum element, also highly biocompatible, provided with a reinforcing mesh which allows stitching of the urethra on said hollow conical frustum element in a more efficient and secure manner without possible breakages of the same element occurring.

In practice said prosthesis is mainly characterised in that said conical frustum is in mesh-reinforced silicone and in that said tubular elements contain internally a plurality of projections suitable for restraining said ureters after their forced fit without having to resort to stitching.

BRIEF DESCRIPTION OF THE DRAWING FIGURES

Further features of the invention will be made clearer by the following detailed description, referred to one of its embodiments purely by way of an example and therefore not limiting, illustrated in the accompanying drawings in which:

FIG. 1a) is a front view of a precursor of a multilayer orthotopic artificial bladder prosthesis of one embodiment;

FIG. 1b) is a sectioned view of FIG. 1a taken along line B-B;

FIGS. 1c), 1d), 1e) are sectioned views of the details denoted respectively by C, D, E in FIG. 1b);

FIG. 2 is an enlarged cross-section view of a portion of the precursor of FIG. 1 of artificial bladder;

DETAILED DESCRIPTION OF THE INVENTION

Figure 1:
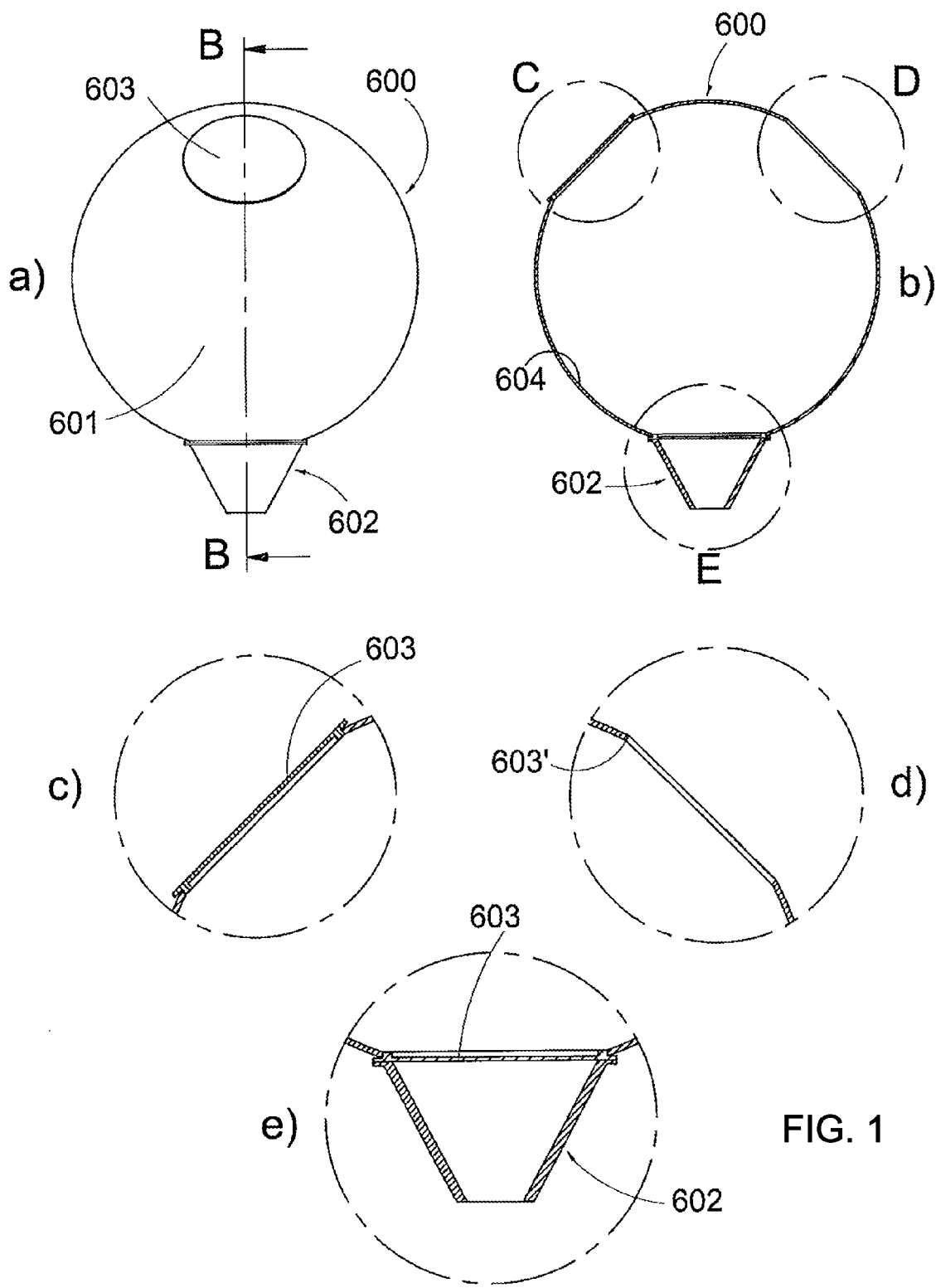
FIG. 1f is an enlarged sectioned view of the conical frustum of FIG. 1e before being glued.
FIGS. 1g and 1h are perspective views of the conical frustum of FIG. 1f.

FIG. 1a illustrates a precursor of prosthesis in the form of a balloon 600. Said balloon 600 is collapsible so that the filling and emptying mechanism of the prosthesis, derived therefrom, functions due to the effect of the differences in pressure between the air inside the prosthesis and the air outside the prosthesis. The capacity of said prosthesis is between 500 and 900 cm$^3$.

Said balloon 600 is made up of a multilayer membrane 2 (FIG. 2) made in soft silicone, with a thickness of approximately 600 microns so as to be compressible, subsiding or collapsible as mentioned above. The membrane of the balloon 600 is preferably made up of 20 layers of silicone, each one having a thickness of approximately 30 microns. Said membrane 2 is preferably made with the method described in the patent application WO 2007/039159 incorporated here by reference.

More particularly the multilayer membrane 2 is obtained from silicone as raw material, by means of a manufacturing procedure known as dipping. By means of machinery known in fact as dipping equipment, a balloon or sac is created from a single layer of silicone and by superimposing on each layer other layers until the required thickness is obtained, for example approximately 600 microns.

This multilayer dipping technique consists in forming the first layer, making it evaporate with cyclohexane for 10 minutes, superimposing the second layer, making it evaporate again with cyclohexane for 10 minutes, and so on up to the final layer. At this point the layered membrane 2 of silicone is in a semifluid state and is then placed in the oven for vulcanization, at a temperature of approximately 150° C. and for a time varying from 30 min to 1 h, on the basis of the size of the prosthesis to be produced. After the vulcanization cycle the multilayer membrane 2 of silicone is in its optimal consistency of softness and elasticity, and no longer in a semifluid state.

The silicone used may consist, for example, of copolymers of dimethyl and methyl-vinyl siloxane, reinforced with silica. A medical silicone is preferably used, such as for example the one known by the code MED 4735™ and marketed by the firm Nusil Technology.

Moreover radio-opacity additives are preferably added to said silicone, such as barium sulphate, titanium dioxide and the like, to allow the detection of the prosthesis with the techniques normally used such as X rays, ultrasound scan, etc.

In a preferred embodiment said balloon 600 has a thickness of 0.6 mm and a diameter between 72 and 74 mm approximately.

On said balloon 600 a longitudinal aperture (not illustrated) and three circular holes 603' (FIG. 1d) are formed and which identify three substantially flat zones, each zone provided with stopper cover 603 (FIGS. 1a and 1c). In a preferred embodiment said holes 603' have a diameter of approximately 22 mm and said stoppers 603 have an external diameter of approximately 26 mm.

After the obtaining of said balloon 600, a circular conical frustum 602 (FIG. 1a), hollow on the inside and facing towards the outer surface 601 of said balloon 600, is glued at one of the three stoppers 603. In a preferred embodiment the conical frustum 602 has a height of approximately 15 mm, a base with diameter of approximately 24 mm, an internal diameter of the hole of approximately 6 mm and a thickness of approximately 1 mm.

Said circular conical frustum 602 is made in reinforced silicone 5 and serves as a guide for insertion of the urethra during the operation as will be described herein below.

The reinforced silicone 5 of said conical frustum 602 is reinforced internally with a mesh or net in Dacron inserted in the thickness and is obtained by a known technique, for example moulding, dipping or similar techniques which allow said mesh to be incorporated in a layer of silicone.

This mesh allows the urethra (not illustrated) to be stitched better to the lateral surface of the conical frustum 602, avoiding possible tearing. Since the suture thread has a size of 4-0 Charrier it is more rigid compared to a cone in silicone alone with thickness of 1 mm as defined above. The presence of a mesh also offers greater points of attachment for the stitches of said urethra to the artificial prosthesis deriving from said balloon 600.

Figure 7:
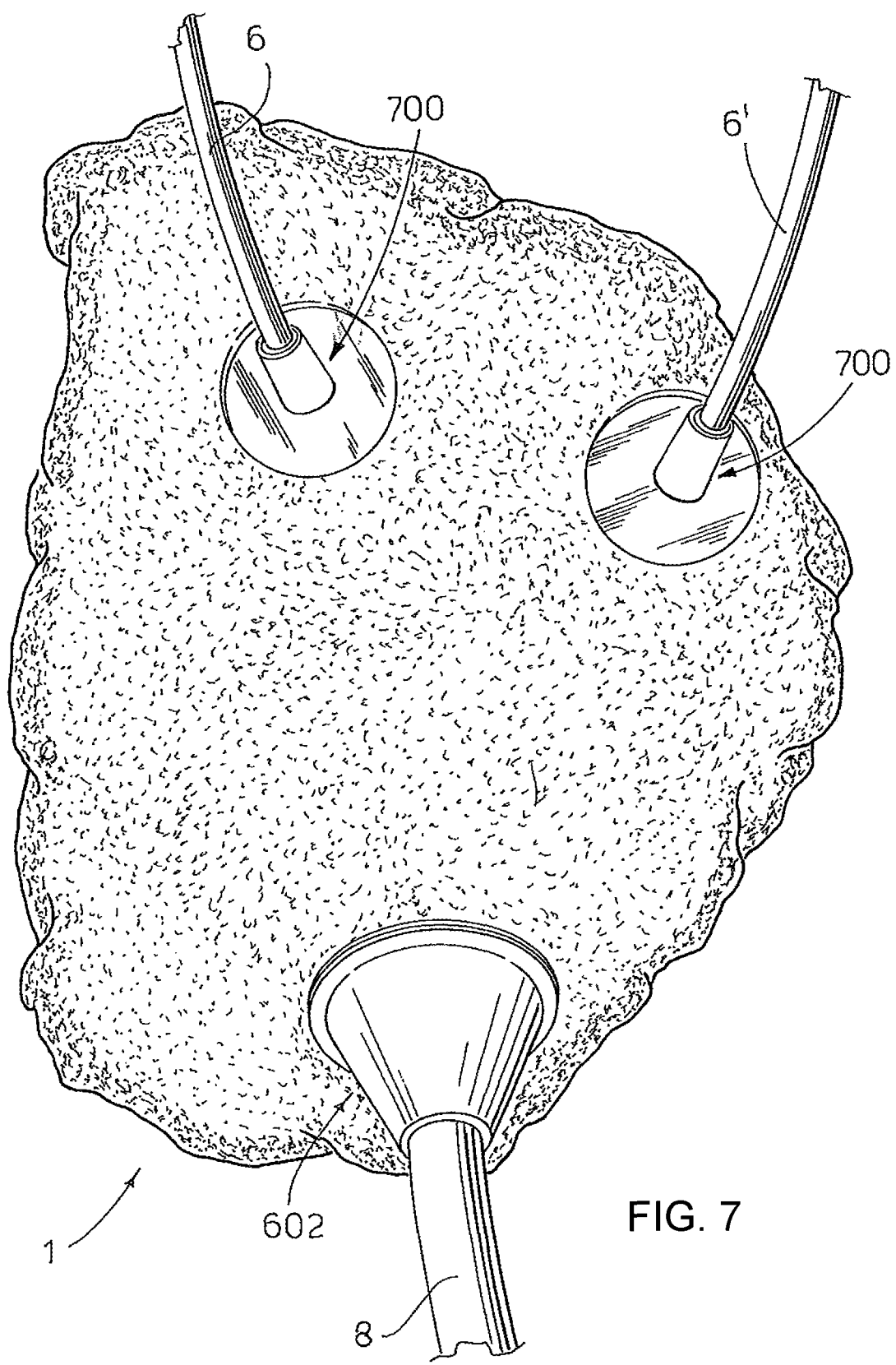
FIG. 7 is a perspective view of an orthotopic artificial bladder prosthesis wherein the ureters and the urethra connected to the artificial bladder are shown.

The other two flattened circular zones at the two stoppers 603, without conical frustum 602, serve instead for the coupling of the ureters 6 (FIG. 7) to said artificial bladder deriving from the balloon 600, by means of respective single body elements 300 (FIG. 3) which will be described in detail further on.

Once the multilayer balloon in silicone 600 having the conical frustum 602 and stoppers 603 has been obtained, application of a microfilm or layer 3 (FIG. 2) of highly biocompatible biomaterial is then carried out on the outermost surface 601 according to the procedure which is to be described in detail later on. The biomaterial is for example pyrolytic turbostratic carbon or diamond-like carbon and the thickness of the layer can be, for example, approximately 0.2-0.3 microns. The internal layer 4 may also be pyrolytic turbostratic carbon or diamond-like carbon is present in the form of an external with a thickness of about 0.2-0.3 micron.

In this way the risk is avoided both of adherence of the fibrotic capsule to the prosthesis and the internal corrosion of said prosthesis due to the action of the urine in respect of the non-coated silicone.

Amorphous diamond-like carbon is a carbon coating, white or transparent, with stratified structure similar to diamond (it is in fact called "diamond-like carbon" (DLC)) with outstanding features of surface resistance such as hardness and resistance to abrasions, in addition to being tolerated well by the skin.

Said amorphous material, in addition to creating smooth surfaces, has been found to be a highly biocompatible material and resistant to urine.

In particular it has been found that this biomaterial is hydrophobic to such an extent as to ensure high slide of the urine which entails a substantial lack of encrustations. Moreover said amorphous diamond-like carbon is found to be neutral when in contact with cells and micro-organisms: this entails a rapid population of the cells and accelerated assimilation of the device implanted. At the same time the adhesion to the surrounding tissues is reduced due to the reduced interaction between the coated surface and the cells of these tissues.

It is also possible to use amorphous diamond-like carbon when appropriately "doped" with various compounds for greater or lesser water repellence.

Pyrolytic turbostratic carbon or diamond-like carbon is deposited on the outer surface 601 according to the known technique, after having shielded only the edges of the aperture mentioned previously, then proceeding with a first vulcanization of said balloon 600.

In this way the balloon 600 is obtained, provided with the conical frustum 602 with the outer surface 601 coated with pyrolytic turbostratic carbon or diamond-like carbon, like the lateral surface of the conical frustum 602. Subsequently a first turning inside out of said balloon 600 is performed through the aperture (not shown in the drawing) in order to bring the surface 601 and said conical frustum 602 from the exterior to the interior of the balloon 600.

At this point the inner surface 604 (FIG. 1b), opposite the surface 601, is turned towards the outside: coating of said surface 604 is then performed by application of a layer 4 of pyrolytic turbostratic carbon, or diamond-like carbon, after suitable shielding of the surfaces of the stoppers 603, now turned towards the outside, and of the edges of the aperture for the turning inside out.

It is also possible, in accordance with the invention, for the outer surfaces of the prosthesis to be coated with pyrolytic turbostratic carbon and the inner ones with diamond-like carbon, or vice versa.

Subsequently a second vulcanization is performed after which the shielding of the surfaces of the stoppers 603 (FIG. 1c) is removed.

At this point a through hole 9 (or 9') (FIG. 3) can be made on one or on both the surfaces of the stoppers 603 without conical frustum 602, preferably using a stylet in stainless steel for brain surgery or a punch.

The hole 9 has a size generally comprised between 5 and 15 of the size in Ch and is such as to allow the insertion and the forced passage of the tubular portion 10 of each hollow element 300, after also having been coated with pyrolytic turbostratic or diamond-like carbon.

In fact said single-body hollow element 300 is also coated with pyrolytic turbostratic carbon or diamond-like carbon, both internally and externally, similarly to what is performed on the balloon 600, shielding both the surface 13 and the edges of the longitudinal cut made previously, then applying the pyrolytic turbostratic carbon, or the diamond-like carbon, on both the surfaces of the hollow element 300 which has been cut longitudinally and opened, vulcanizing and removing subsequently the shielding of the edges of the cut in order to be able to perform gluing of said two shielded edges in order to restore the initial shape of the element 300.

Subsequently gluing is performed of the surface 13 of the conical frustum 14 of said hollow element 300 to the surface 605 (FIG. 4) of the stopper 603 not coated with pyrolytic turbostratic carbon or with diamond-like carbon.

At the end of gluing, each element 300 has its own conical frustum part 14 turned towards the outside of the balloon 600 and the tubular part 10 turned towards the inside.

Figure 4:
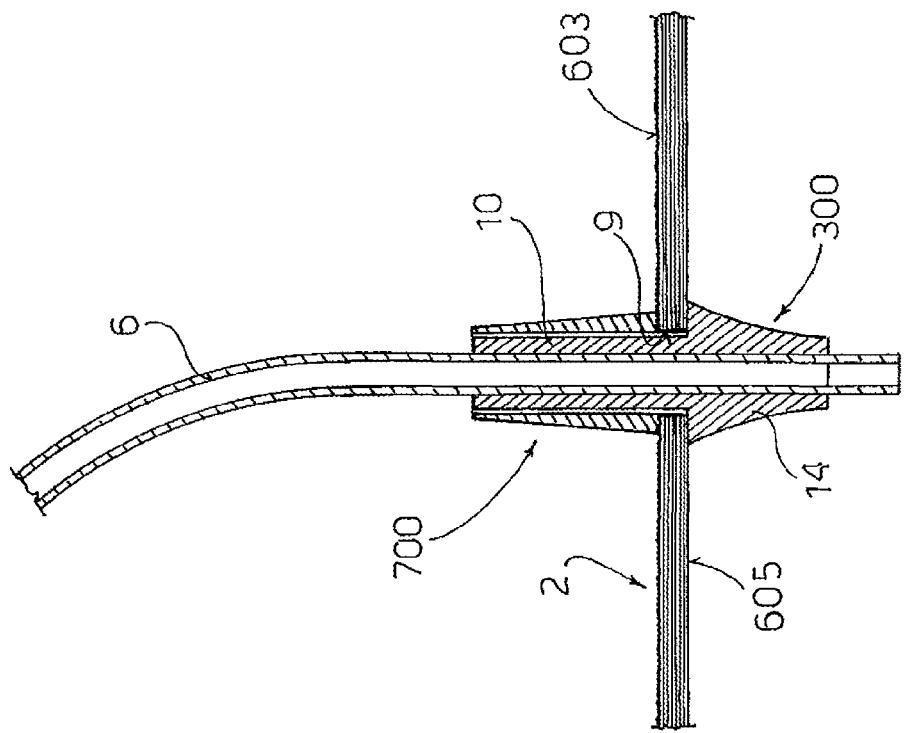
FIG. 4 is an enlarged view in median section of the ureter after attachment to an artificial prosthesis according to the invention.

At this point, after having performed coupling of one or two elements 300 with the balloon artificial bladder 600, the balloon 600 is once again turned inside out, then returning to the situation illustrated in FIGS. 1a and 4 where the surface 601, the conical frustum 602 and the tubular part 10 of each of said elements 300 are turned towards the outside while the conical frustum part 14 of the element 300, the surface 604 of the balloon and the surface 605 of the stoppers 603 are turned towards the inside of the balloon 600.

At this point it is possible to proceed with gluing together of the edges of the aperture of turning inside out in order to obtain a closed balloon 600 and therefore a closed bladder. The gluings mentioned above are performed preferably with a silicone glue.

The tubular element 300 is illustrated in detail in FIGS. 5a-5d. Said element 300 is a single body and has a tubular portion 10 wherein the ureter 6 is to be forced-fitted (FIGS. 3-4) and a frustoconical portion 14 connected to said tubular portion 10 by means of a circular surface 13 (FIG. 5b) whose purpose is to allow the gluing of said element 300 to the inner surface of the artificial bladder. Said element 300 is made in silicone, preferably radiopaque, with approximately 50 Shore hardness.

In a preferred embodiment of said element 300, the tubular element 10 has an internal diameter of approximately 7 mm and an external diameter of approximately 8 mm, a total length of approximately 40 mm, a diameter of the circular surface 13 equal to approximately 16 mm and a length of the tubular part 10 of approximately 30 mm. Said tubular portion 10 is normally perpendicular to said flat base 13.

Inside said hollow conic element 300, both in the tubular portion 10 and in the conical frustum portion 14, there is a plurality of projections or teeth 16 in order to avoid withdrawal of the ureters 6 (FIG. 4) from said element 300: since during the operation the ureters 6 are pulled towards the bladder to allow their insertion inside the tubular body of the hollow conic element 300, it is possible that, the operation having ended, they return into the initial position, moving towards the kidneys, which may cause the withdrawal of said ureters 6,6' (FIG. 7) from said element 300.

Figure 5A:
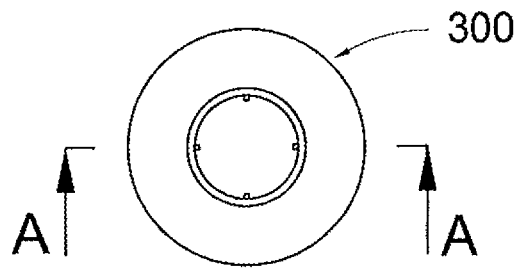
FIG. 5a is a view from above of an embodiment of the hollow conic element.
Figure 5D:
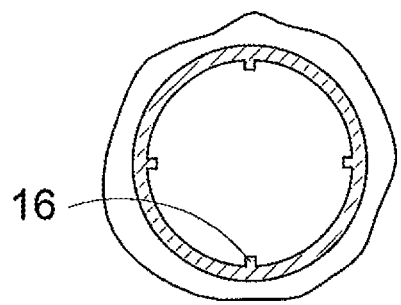
FIG. 5d is a partially interrupted horizontal section view of the hollow conic element of FIG. 5b taken along line D-D.
Figure 5B:
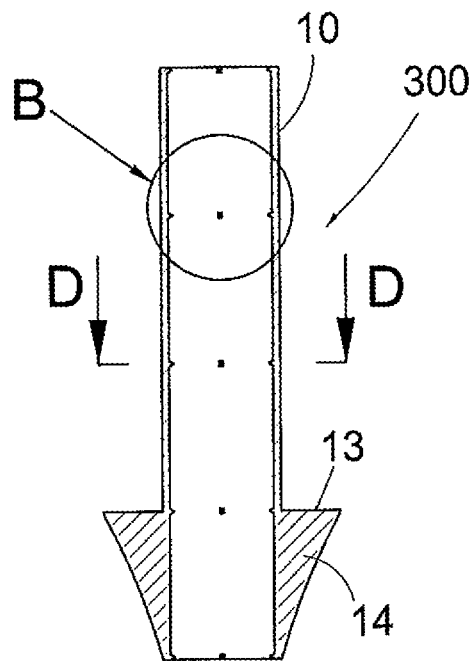
FIG. 5b is a vertical median section view of the hollow conic element of FIG. 5a taken along line A-A.

Two pairs of teeth 16 are arranged approximately every 10 mm (FIG. 5b) in a longitudinal direction and diametrically opposite one in relation to the other in horizontal section (FIG. 5b). In horizontal section said teeth 16 project in such a way as to define a circumference whose diameter is smaller compared to the diameter of the ureter 6,6' so as to have a coupling with interference (forced-fit).

In this way the tubular portion 10 of the hollow element 300 will also go to tighten slightly around the tube of the ureter 6,6', also due to its elasticity. In this way it is no longer necessary to attach the ureter 6,6' to the portions of membrane of artificial bladder by means of suture stitches as instead occurs in the prior art.

In a preferred embodiment each tooth 16 has a height of 1 Ch and width of 1 Ch.

The overall number of teeth 16 is at least four, even if this is not binding for the purposes of the present invention.

With the process described up to this point an orthotopic prosthesis 1 (FIG. 7) of artificial bladder 600 is obtained, coated both internally and externally with pyrolytic turbostratic carbon, or diamond-like carbon, with the conical frustum 602 and the tubular part 10 of the single body element 300 turned towards the outside, which is ready to be implanted in the patient.

During the operation the conical frustum 602 will be traversed by a punch or stylet in stainless steel for brain surgery in order to perforate the stopper 603 under the conical frustum 602 and allow the urethra 8 (FIG. 7) to enter the artificial bladder while each ureter 6, 6' will be forced inside said tubular part 10.

Figure 3:
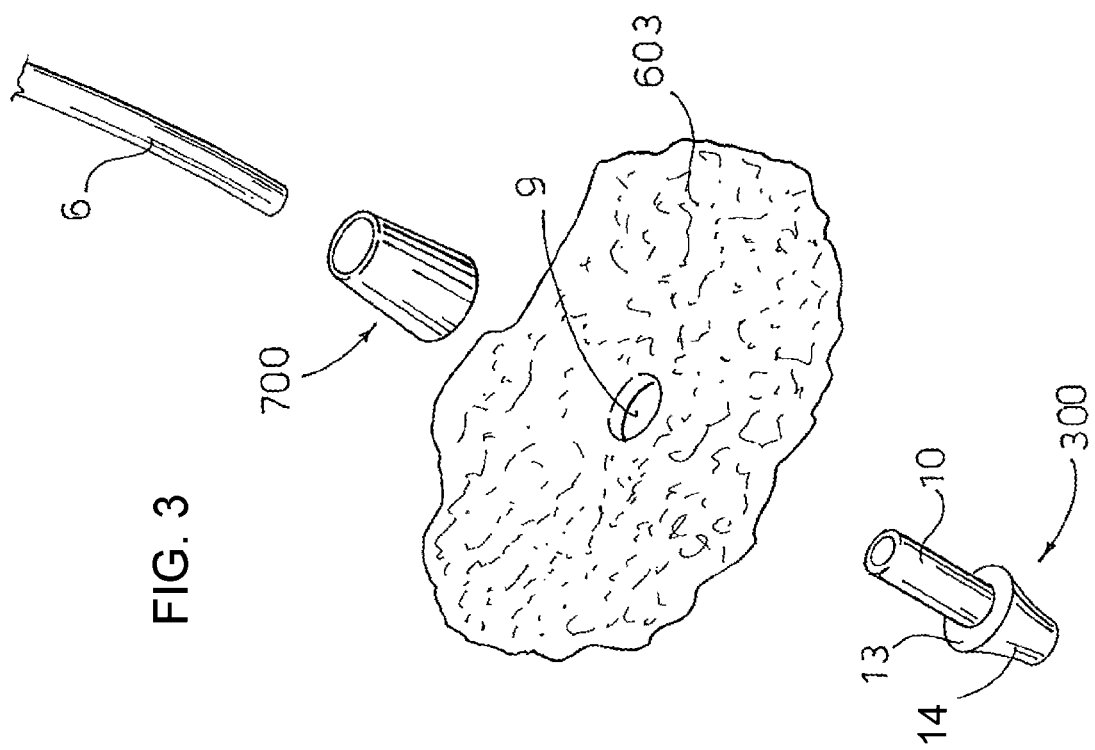
FIG. 3 is a blown-up and cross-section perspective view showing the assembly between a ureter and the prosthesis by means of a hollow conic element and a sleeve.
Figure 6A:
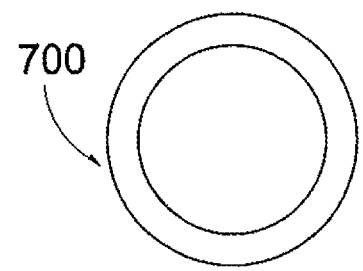
FIGS. 6a and 6b are respectively a view from above and in median section of a sleeve, illustrated in FIG. 3 and to be coupled to the hollow conic element of FIGS. 5a-5d.
Figure 5C:
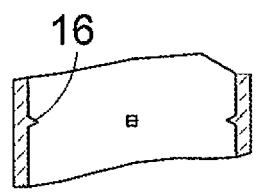
FIG. 5c is an enlarged median section view of the details denoted respectively by B in FIG. 5b.
Figure 6B:
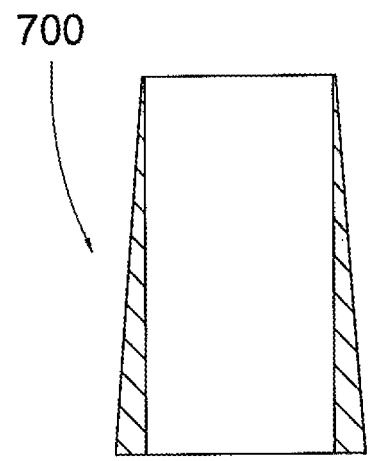

In order to provide greater protection for the ureter 6,6' inserted in said tubular portion 10 of said single part element 300, and a greater rigidity for said tubular portion 10, it is preferable to use also a sleeve 700 (FIGS. 3 and 6) to be applied externally to the tubular portion 10 of the element 300 as illustrated in FIG. 3, once the ureter 6, 6' is inserted.

With the process described up to this point it is therefore possible to obtain a prosthesis 1 according to the invention where the artificial bladder 1 is made from a balloon 600 in radiopaque silicone coated internally and externally with pyrolytic turbostratic carbon, or diamond-like carbon, which also comprises a conical frustum 602 in reinforced silicone suitable for the connection of said prosthesis 1 to said urethra 8. Said balloon also provides for the attachment of the ureters 6,6' by means of a single body hollow element 300 coated internally and externally with pyrolytic turbostratic carbon, or diamond-like carbon, which is formed from a frustoconical portion 14 in addition to the widened base 13 which is connected to the tubular portion 10 which will go to insert in the through holes 9,9' formed in the membranes 603' of said balloon while the widened base 13 of the element 300 will come into contact with the inner surface 605 of said membrane 2.

Numerous detail modifications and changes may be made to the present embodiment which are within the reach of a person skilled in the art and in any case coming within the scope of the invention expressed by the annexed claims.

The invention claimed is:

1. An orthotopic artificial bladder prosthesis (1) comprising a collapsible balloon (600) made of a silicone multi-layer membrane (2) having an outer surface (601) and an inner surface (604) both coated with a coating selected from the group consisting of pyrolytic turbostratic carbon and diamond-like carbon, provided with two tubular elements (10) extending outwards adapted for connecting ureters (6, 6') to said prosthesis (1) by means of a forced fit, and with a conical frustum (602) suitable for connecting an urethra (8) to said prosthesis,
   wherein said conical frustum (602) is made of a mesh-reinforced silicone (5) and said tubular elements (10) contain internally a plurality of projections (16) adapted to detain said ureters (6,6') after being fitted forcedly, and
   wherein each tubular element (10) is a tubular portion of a hollow conic element (300) coated internally and externally with a coating selected from the group consisting of pyrolytic turbostratic carbon and diamond-like carbon, and it is connected to a frustoconical portion (14) having a widened base (13) adapted to be glued to the inner surface of the balloon (600) so as to render said hollow conic element (300) integral with said balloon (600).

2. Prosthesis according to claim 1, wherein radio-opacity additives are added to the silicone of the membrane (2).

3. Prosthesis according to claim 1, further comprising at least two holes (9,9'), each of said holes being formed on a respective stopper cover (603) that is on said balloon, each of said holes (9,9') being adapted for allowing the insertion of the tubular portion (10) of the hollow element (300).

4. Prosthesis according to claim 1, wherein said multilayer membrane (2) has a thickness of about 600 micron and is formed by twenty silicone layers.

5. Prosthesis according to claim 1, wherein pyrolytic turbostratic carbon or diamond-like carbon is present in the form of an external layer (3) and internal layer (4), each layer having a thickness of about 0.2-0.3 micron.

6. Prosthesis according to claim 1, wherein each of said tubular elements (10) and each hollow conic element (300) are made of silicone.

7. Prosthesis according to claim 1, wherein said projections (16) project in such a way to define, in horizontal section, a circumference having a diameter smaller than the diameter of ureters (6,6') in order to tighten said ureters.

8. Prosthesis according to claim 1, wherein surfaces of the prosthesis directed outwardly are coated with pyrolytic turbostratic carbon and those directed inwardly are coated with diamond-like carbon, or vice versa.

9. Prosthesis according to claim 3, wherein radio-opacity additives are added to the silicone of the membrane (2).

10. Prosthesis according to claim 2, further comprising at least two holes (9,9'), each of said holes being formed on a respective stopper cover (603) that is on said balloon, each of said holes (9,9') being adapted for allowing the insertion of the tubular element portion (10) of the hollow element (300).

11. Prosthesis according to claim 1, wherein said multi-layer membrane (2) has a thickness of about 600 micron.

12. Prosthesis according to claim 2, wherein said multi-layer membrane (2) has a thickness of about 600 micron and is formed by twenty silicone layers.

13. Prosthesis according to claim 3, wherein said multi-layer membrane (2) has a thickness of about 600 micron and is formed by twenty silicone layers.

14. Prosthesis according to claim 1, wherein radio-opacity additives selected from the group consisting of barium sulphate and titanium dioxide are added to the silicone of the membrane (2).

15. Prosthesis according to claim 1, wherein each of said tubular elements (10) is made of radiopaque silicone having 50 Shore hardness.

16. Prosthesis according to claim 1, wherein each said hollow conic element (300) is made of radiopaque silicone having 50 Shore hardness.

17. Prosthesis according to claim 1, wherein said projections (16) project in such a way to define, in horizontal section, a circumference having a diameter smaller than the diameter of ureters (6,6') in order to tighten said ureters, said projections having a width of 1 Ch and a height of 1 Ch.

18. Prosthesis according to claim 3, wherein radio-opacity additives selected from the group consisting of barium sulphate and titanium dioxide are added to the silicone of the membrane (2).

\* \* \* \* \*